United States Patent [19]

Euvrard

[11] Patent Number: 4,477,253

[45] Date of Patent: Oct. 16, 1984

[54] DEVICE FOR QUICK COUPLING OF DENTAL APPLIANCE

[75] Inventor: Hubert Euvrard, Geneuille, France

[73] Assignee: Micro-Mega S.A., Besancon, France

[21] Appl. No.: 392,000

[22] Filed: Jun. 25, 1982

[30] Foreign Application Priority Data

Jun. 30, 1981 [FR] France .............................. 81 12998

[51] Int. Cl.³ .............................................. A61C 1/08
[52] U.S. Cl. .................................................. 433/126
[58] Field of Search ..................... 433/126; 24/221 R; 285/401, 402, 360, 361, 376, 396

[56] References Cited

U.S. PATENT DOCUMENTS 3,029,093 4/1962 Willis ................................... 285/376
4,175,323 11/1979 Eibofner et al. ..................... 433/126

*Primary Examiner*—Robert Peshock
*Attorney, Agent, or Firm*—Robert E. Burns; Emmanuel J. Lobato; Bruce L. Adams

[57] ABSTRACT

Device for high-speed coupling between a dentistry appliance and an element to which it is connected during use by the practitioner, characterised in that it comprises essentially:

(a) a collar (6) truncated over at least one segment (7) and fixed to the dentistry appliance;
(b) a ring (12) fixed to said element, the end (14) of which is recessed to form a female shape into which the profile of said collar can fit, the connection being obtained as a result of the positioning of the collar (6), after it has penetrated into said recess (14), in a groove (15) in the ring as a result of relative rotation of the collar and the ring.

Application to the connection of dentistry articles.

3 Claims, 5 Drawing Figures

DEVICE FOR QUICK COUPLING OF DENTAL APPLIANCE

BACKGROUND OF THE INVENTION

The subject of the present invention is a device for high-speed coupling between a dentistry appliance and an element to which it is connected during use by the practitioner.

Devices of this type are already known, especially for connection between a flexible supply line and dentistry appliances such as, but not restricted to, turbines, air motors, scalers or the like.

All these appliances are used by the dental surgeon and it is sometimes necessary to change them during treatment.

The couplings used at the present time are screw fittings which consequently require a relatively long time to change, which is obviously a disadvantage for the user.

SUMMARY OF THE INVENTION

The aim of the invention is to overcome this disadvantage by proposing a connection which makes it possible to attach or remove a dentistry appliance quickly to or from the element on which it is to be positioned.

According to the invention, this result is obtained by means of a device for high-speed coupling between a dentistry appliance and an element to which it is connected during use by the practitioner, characterized in that it comprises essentially:

(a) a collar truncated over at least one segment and fixed to the dentistry appliance, (b) a ring fixed to said element, the end of which is recessed to form a female shape into which the profile of said collar can fit, the connection being obtained as a result of the positioning of the collar, after it has penetrated into said recess, in a groove in the ring as a result of relative rotation of the collar and the ring. The connection then has a mechanical elastic seal.

The connection device will preferably be used for connecting a dentistry appliance possessing inner fluid-circulation tubes to a flexible line supplying said fluids such as water and compressed air.

In this case, the various fluid feed tubes will be joined via a seal made of synthetic material compressed during the relative rotation of the two elements of the connection or during penetration of the collar into the recess in the ring.

The collar will advantageously possess on its periphery and on its face farther away from the ring a sloping surface which, by interacting, during the relatve rotation of the two elements of the connection, with one of the radial walls of the groove in the ring, will ensure that the two elements of the connection are fixed rigidly to one another.

BRIEF DESCRIPTION OF THE DRAWING

The invention will be understood better from the description which follows of a non-limiting embodiment with reference to the attached drawings in which.

DESCRIPTION OF THE PREFERRED EMBODIMENT

Reference will be made below to the example of the connection of an air motor, but purely by way of illustration.

The motor (1) is provided in its rear part with a cylindrical projection (2) to the end of which a sealing gasket (3) is fixed. Two pipes for feeding fluids to the motor, (4) and (5) respectively, open onto the front face of the projection or adapt (2).

Figure 1:
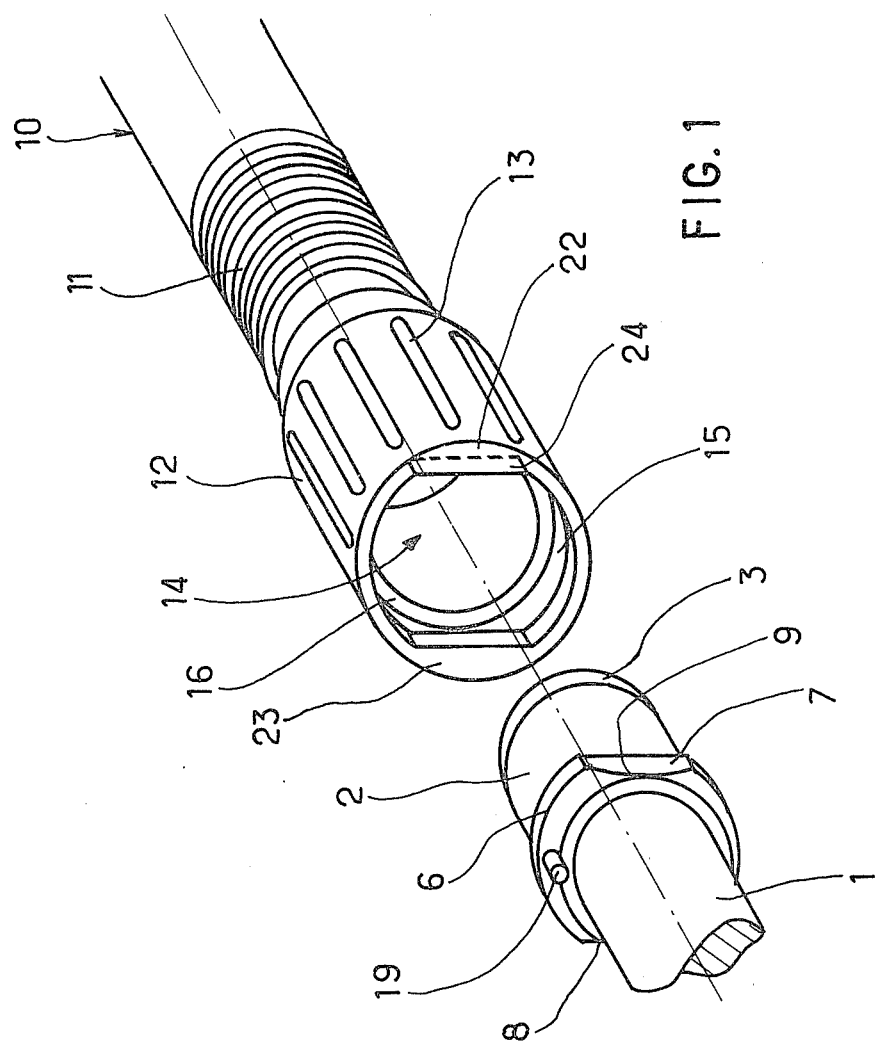
FIG. 1 is a perspective view of the two elements of the device according to the invention before they are fitted into one another, in the case of connection to a fluid-supply line.
Figure 3:
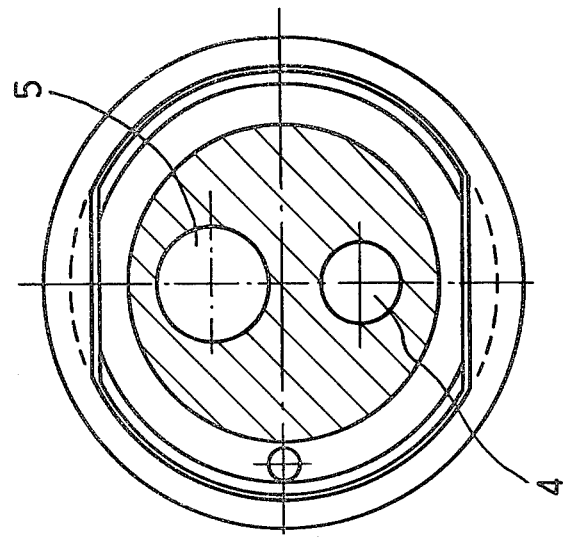
FIG. 3 is a view in a section along the line G—G of FIG. 2.
Figure 2:
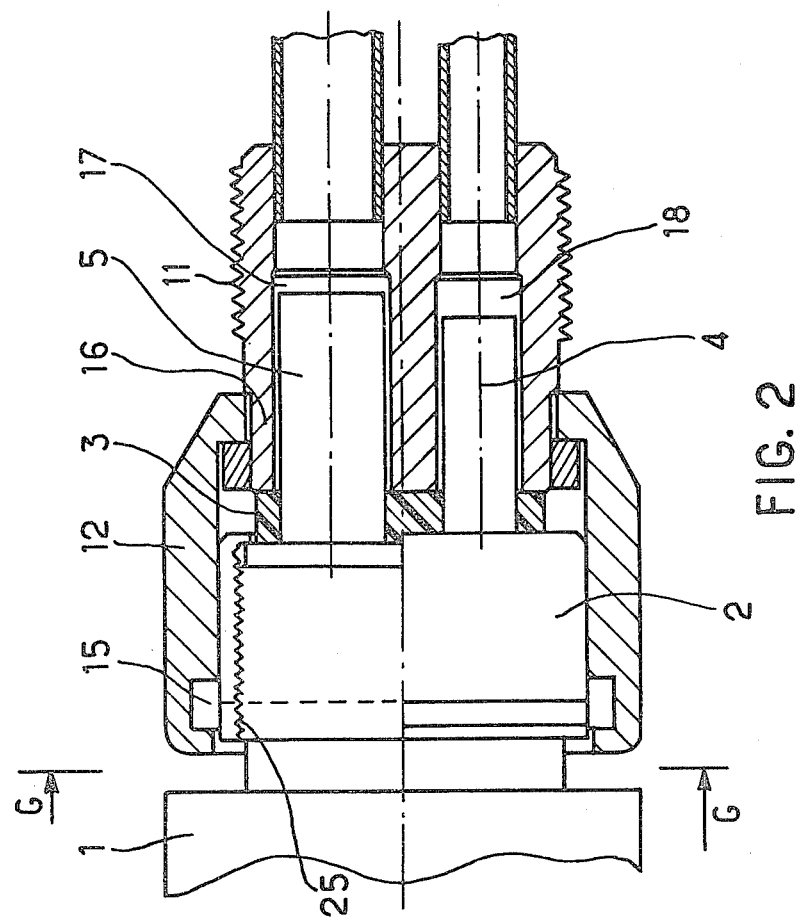
FIG. 2 is a sectional view of the connection device in an intermediate position after the collar has been introduced into the recess in the ring.
Figure 5:
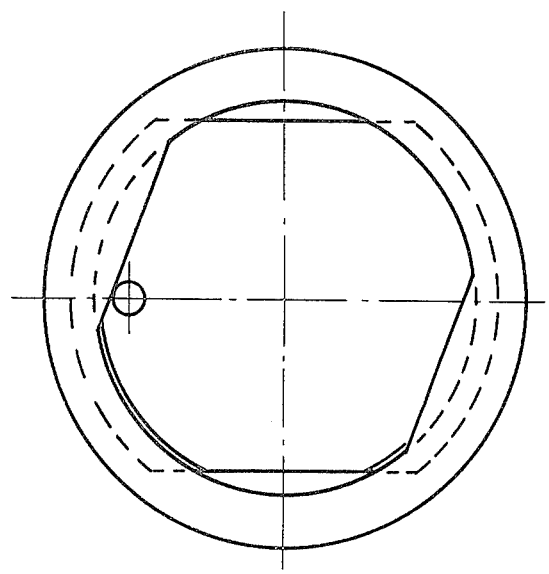
FIG. 5 is a view in a partial section along the line F—F of FIG. 4.
Figure 4:
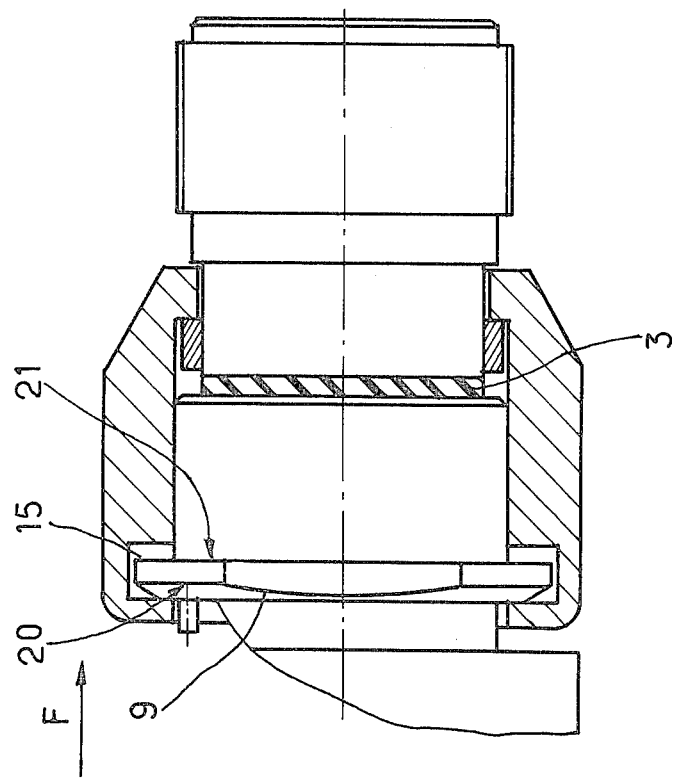
FIG. 4 is a view similar to FIG. 2, in the locking position.

Set back in relation to the projection (2) the motor has, according to the invention, a collar (6), at least one segment (7) of which is flat or truncated. FIG. 1 illustrates a collar having two symmetrical truncated segments (7,8), but it should be understood that this is in no way limiting, and any contour of the collar compatible with the use to be described must be understood as coming within the scope of the present invention.

The collar (6) has on the same side as the element to be connected to the dentistry appliance a face (21) perpendicular to the longitudinal axis of the connection, the face (20) on the same side as the motor assuming a conical profile.

On its face farther away from the line, the collar (6) has at least one sloping surface (9), the function of which will be explained below.

This sloping surface is formed by the intersection between the straight plane parallel to the longitudinal axis of the connection corresponding to the truncated segment (7) and the cone formed by the chamfer face (20). This sloping surface is, in the present case, the edge formed by the intersection of these two faces.

The projection (2) of the motor and the collar (6) constitute the male element of a connection, the female element of which is now described.

Fixed to the supply line (10) is a connector (11) on which pivots a ring (12) having on its periphery notches (13) making it easier for the user to hold it and grip it.

The front end of the ring (12) has a recess (14) the contour of which corresponds to that of the collar (6) or at least corresponds to a profile into which that of the collar (6) can fit.

Advantageously, the two contours will be exactly complementary, but the provision of two contours which can fit into one another but are exactly complementary would not depart from the scope of the invention.

The ring (12) also has an annular groove (15) in which the collar (6) will be received.

The device operates as follows:

the two elements (6) and (14) are brought in line with one another;

the projection (2) is introduced into the ring (12) until the gasket (3) comes in contact with the end (16) of the line (10);

the tubes (4) and (5) then penetrate into the receptacles (17,18) provided for this purpose in the end (16);

the collar (6) and the ring (12) are then rotated relative to one another.

This rotation brings the inner edge (22) of the sectors (23,24) in contact with the edge (9), the number and shape of these corresponding to those of the truncated segments (7). The edge (22) slips very easily over the sloping surface (9) and compresses the gasket (3) without strain. The two parts are then fixed to one another.

In order that rotation cannot continue so as to return finally to the unlocking position, a stop-pin (19) is located on the face of the collar (6) having the sloping surface (9).

Locking and unlocking is carried out, in practice, as a result of simple rotation of the ring (12) in one direction or the other.

To great advantage, these connections can be obtained from screw connections of the prior art.

For this purpose, it is sufficient to screw onto the thread (25) of a screw connection the projection (2) which has just been described and which possesses the gasket (3) and the collar (6).

The scope of the invention even includes the provision of a ring on the projection of the motor and of the collar on the head of the line, or any other combination of the various elements of the connection.

I claim:

1. A device for quick coupling and decoupling of a dental appliance and a supply line comprising, a threaded elongated adapter threadable onto a dental appliance for quick coupling and decoupling of the dental applicance and a supply line, a collar disposed circumferentially of the adapter and having a truncated segment, a connector fitted on the supply line and having a tubular ring rotatably mounted on the connector for receiving the adapter inserted axially therein, the tubular ring having an opening and configured internally complementary to the periphery of the collar for entry of the collar internally of the tubular ring when properly aligned with said opening, the tubular ring having an internal groove for receiving the collar when the adapter is inserted into axial position in the tubular ring and the tubular ring rotated relative to the collar out of registry with said truncated segment thereof to receive it in said groove and house it therein releasably coupling the adapter and the tubular ring and said collar on said adapter having a resilient portion thereof thicker than the width of said groove thereby to releasably hold the tubular ring from rotating relative to the collar.

2. A device for quick coupling and decoupling of a dental appliance and a supply line according to claim 1, in which said adapter has two conduits therein extending axially therefrom, and in which said connector has two axial recesses into which said conduits extend for making a fluid connection to fluid sources in communication with said recesses.

3. A device for quick coupling and decoupling of a dental appliance and a supply line according to claim 2, including a sealing gasket on an end of said adapter inserted into said tubular ring and through which said two conduits extend axially, and the connector having a surface which said sealing gasket abuts and effects a seal about said fluid connection.

* * * * *